United States Patent [19]

Even-Esh

[11] Patent Number: 5,531,750

[45] Date of Patent: Jul. 2, 1996

[54] SURGICAL TOOL AND ADJUSTABLE LOCKING HANDLE THEREFOR

[75] Inventor: Alexander Even-Esh, Edison, N.J.

[73] Assignee: Snap-on Incorporated, Kenosha, Wis.

[21] Appl. No.: 275,850

[22] Filed: Jul. 15, 1994

[51] Int. Cl.$^6$ .................................................... A61B 17/56
[52] U.S. Cl. ................................................. 606/79; 606/85
[58] Field of Search .......................... 606/79, 85; 81/302, 81/367, 368, 369, 370, 371, 372, 373, 374, 375, 376, 377, 378, 382, 383.5, 384

[56] References Cited

U.S. PATENT DOCUMENTS

| | | | |
|---|---|---|---|
| 1,060,391 | 4/1913 | Wilson | 81/382 |
| 2,598,650 | 5/1952 | Smith et al. | 81/369 |
| 2,822,715 | 2/1958 | Raimondi | 81/383.5 |
| 3,866,494 | 2/1975 | Dotson . | |
| 4,583,270 | 4/1986 | Kenna . | |
| 4,601,289 | 7/1986 | Chiarizzio et al. . | |
| 4,739,750 | 4/1988 | Masse et al. . | |
| 4,765,328 | 8/1988 | Keller et al. . | |
| 4,921,493 | 5/1990 | Webb, Jr. et al. . | |
| 4,963,155 | 10/1990 | Lazzeri et al. . | |
| 4,990,149 | 2/1991 | Fallin . | |
| 5,020,519 | 6/1991 | Hayes et al. . | |
| 5,062,191 | 11/1991 | Carr . | |
| 5,089,003 | 2/1992 | Fallin et al. . | |
| 5,122,130 | 6/1992 | Keller . | |
| 5,174,177 | 12/1992 | Jeromson, Jr. et al. | 81/302 |
| 5,190,549 | 3/1993 | Miller et al. . | |
| 5,190,550 | 3/1993 | Miller et al. . | |
| 5,261,915 | 11/1993 | Durlacher et al. . | |

OTHER PUBLICATIONS

Polaroid photograph of adjustable Vise–Grip Pliers made by Peterson.
Three Polaroid photographs of Kyocera surgical tool and associated locking handle.

Primary Examiner—Stephen C. Pellegrino
Assistant Examiner—Scott B. Markow
Attorney, Agent, or Firm—Emrich & Dithmar

[57] ABSTRACT

An adjustable locking handle securely grips an associated surgical tool for fixing the tool to the handle. The tool has first and second coupling portions, while the handle has an elongated body with fixed and movable jaws thereon respectively adapted for engagement with the first and second coupling portions on the tool. The movable jaw is pivotally movable about a fixed axis between locking and unlocking conditions relative to the fixed jaw by means of a linkage including a locking lever pivotally mounted on the body and a release lever pivotally interconnecting the locking lever and the jaw. A cylindrical cam is disposed in a bore in the locking lever coaxially with the movable pivot axis of the lever, the cam being eccentrically mounted on a headed shaft on the body so that rotation of the shaft shifts the position of the movable pivot axis of the locking lever, thereby shifting the position of the linkage and the movable jaw in the locking and unlocking conditions thereof, to assure firm clamping of the tool, compensating for dimensional variations in the parts. A detent is associated with the shaft head to retain the cam in each of a plurality of rotational positions.

13 Claims, 2 Drawing Sheets

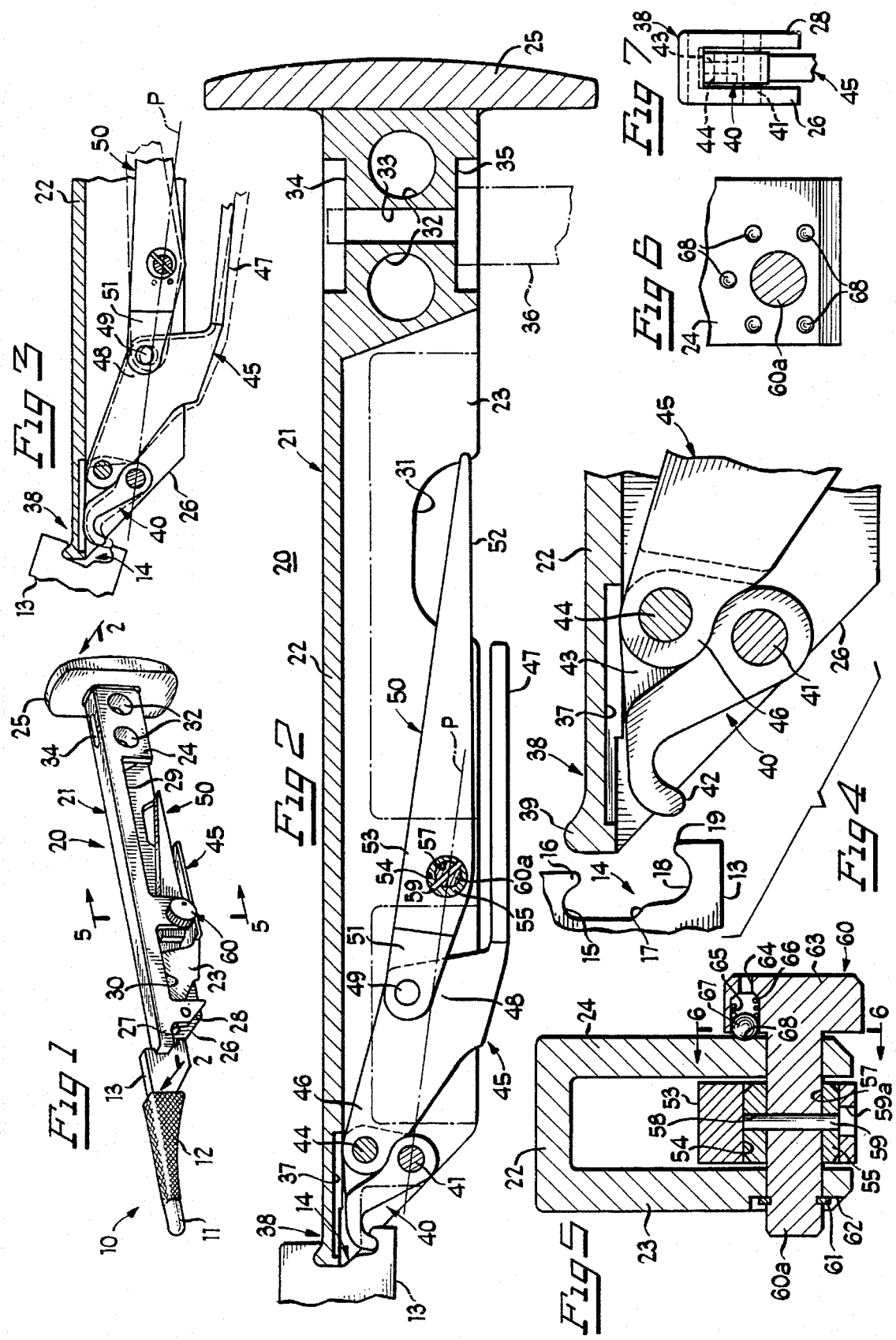

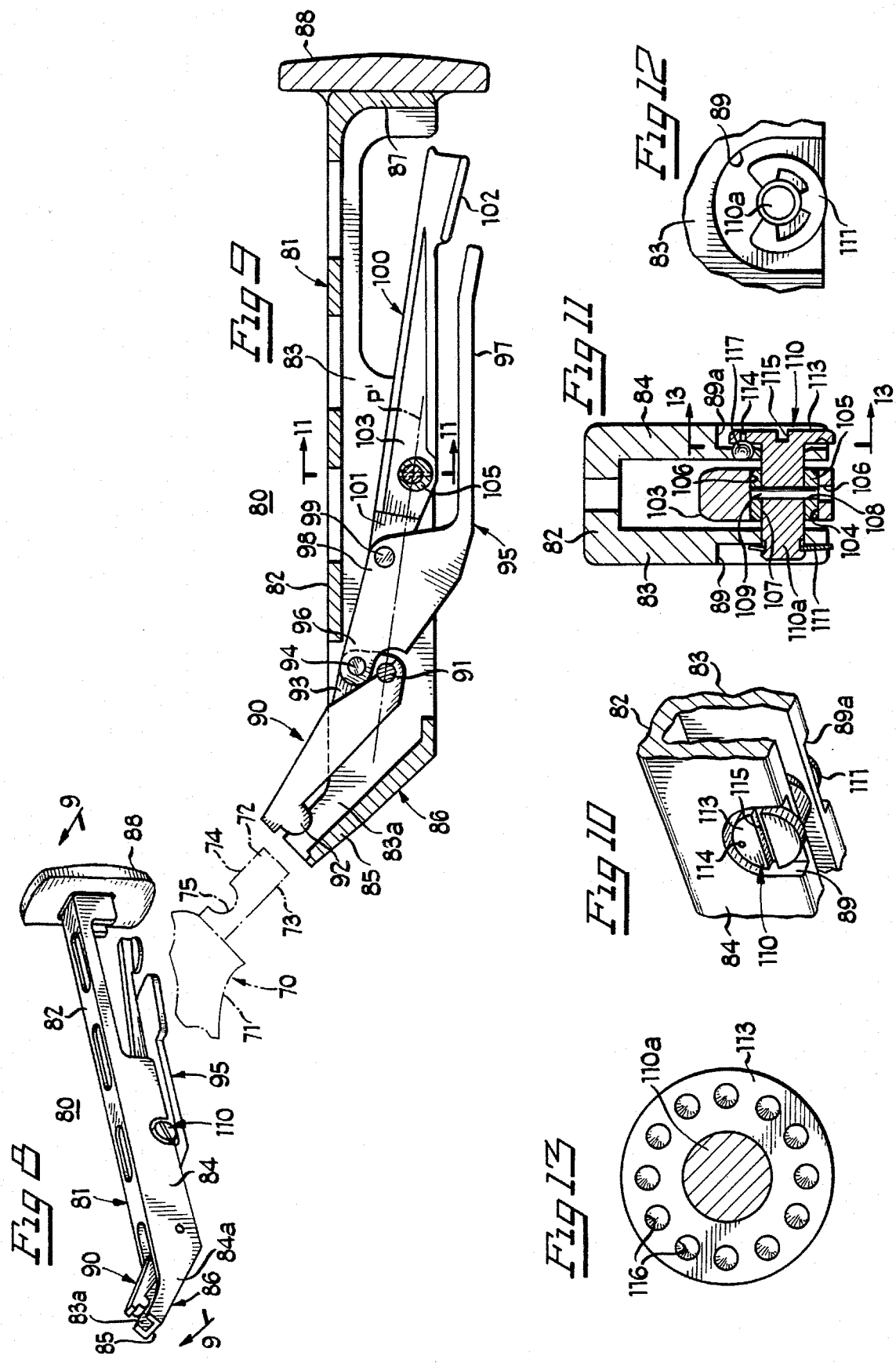

SURGICAL TOOL AND ADJUSTABLE LOCKING HANDLE THEREFOR

BACKGROUND OF THE INVENTION

1. Field of the Invention

This invention relates to surgical instruments and, in particular, to a locking surgical tool/handle system.

2. Description of the Prior Art

In certain surgical procedures it is necessary to drill or ream the intermedullary canal of a bone. For example, in the replacement of a hip joint, it is very often necessary to replace the natural femoral head with a prosthetic stem affixed within the femur. The procedure for implanting the prosthetic stem includes the use of a broach or rasp in preparing the femoral shaft for the reception of the prosthetic stem by providing contouring of the femoral shaft to the gross geometry of the prosthetic stem, thereby assuring accurate location and good fit. In order to facilitate utilization of such a broach or rasp tool, it has heretofore been suggested that the handle of the instrument be selectively detachable from the working portion of the tool to facilitate precise gauging of the location of the tool within the femoral shaft, to facilitate cleaning of the tool, and for other reasons.

A number of detachable handles for use with releasable tools, such as broaches or rasps, have heretofore been provided. However, prior handles have exhibited a number of problems, one of which being that they fail to achieve a tight fit between the tool and the handle, resulting in a loose or wobbly coupling. This impairs good control of the tool during a surgical procedure. In particular, one such prior handle utilizes a clamping arrangement, wherein the tool has coupling portions which co-act with fixed and movable jaws on a handle, the jaws being operated between locking and unlocking conditions by means of an over-center, lever-operated linkage arrangement. However, because of tolerance variations in the manufacture of the handle components and the broaches, they may not interfit in the locking condition of the handle jaws so as to ensure a tight clamping of the tool to immovably fix it on the handle. The resulting looseness or "play", even though slight, can impair effective tool control.

SUMMARY OF THE INVENTION

It is a general object of the invention to provide an improved surgical tool and locking handle therefor which avoid the disadvantages of prior tool-handle combinations, while affording additional structural and operating advantages.

An important feature of the invention is the provision of an adjustable locking handle for a surgical tool which can be adjusted to accommodate slight differences in fit with associated tools.

A further feature of the invention is the provision of a handle of the type set forth which insures a tight gripping of the associated tool.

In connection with the foregoing features, a further feature of the invention is the provision of a handle of the type set forth which is characterized by an over-center lever operation, such that the pivot axis of the lever is shiftable.

Another feature of the invention is the provision if a handle of the type set forth, wherein the adjustment means is provided with detents to resiliently retain the adjustment mechanism in each of a plurality of adjustment positions.

A still further feature of the invention is the provision of a handle of the type set forth, in combination with an associated tool.

These and other features of the invention are attained by providing an adjustable locking handle for a surgical tool comprising: an elongated body having a tool end, two jaws on the body adjacent to the tool end, at least one of the jaws being movable between locking and unlocking conditions of the jaws, a manually operable locking linkage mounted on the body and coupled to at least the one jaw for effecting movement thereof between the locking and unlocking conditions, and a cam member mounted on the body for camming engagement with the linkage and rotatable relative to the body for selectively shifting the position of at least the one jaw in the locking and unlocking conditions.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a perspective view of a surgical tool locked on the end of a handle assembly in accordance with a first embodiment of the present invention;

FIG. 2 is an enlarged, fragmentary view in vertical section taken along the line 2—2 in FIG. 1;

FIG. 3 is a slightly reduced, fragmentary, sectional view of the forward end of the combination illustrated in FIG. 2, showing the surgical tool partially mounted on the handle assembly, and illustrating the jaw linkage of the handle assembly in two different positions, respectively shown in solid and dotted lines, corresponding to two positions of the adjustment knob;

FIG. 4 is a further enlarged, fragmentary, sectional view of the forward end of the handle assembly of FIG. 2, with the surgical tool separated therefrom;

FIG. 5 is an enlarged view in vertical section taken along the line 5—5 in FIG. 1;

FIG. 6 is a fragmentary view in vertical section taken along the line 6—6 in FIG. 5;

FIG. 7 is a fragmentary end elevational view of the handle assembly of FIG. 3, as viewed from the left-end thereof, with the surgical tool removed;

FIG. 8 is a perspective view of a handle assembly in accordance with a second embodiment of the invention;

FIG. 9 is a slightly enlarged view in vertical section taken along the line 9—9 in FIG. 8, and illustrating in phantom an associated surgical tool for coupling thereto;

FIG. 10 is an enlarged, fragmentary, rear perspective view of the adjustment knob portion of the handle assembly of FIG. 8;

FIG. 11 is an enlarged view in vertical section taken along the line 11—11 in FIG. 9;

FIG. 12 is a fragmentary, side elevational view of a portion of the handle assembly of FIG. 8, as viewed from the left-hand side of FIG. 11; and FIG. 13 is an enlarged view in vertical section of the inside of the head of the adjustment knob, taken generally along the line 13—13 in FIG. 11.

DESCRIPTION OF THE PREFERRED EMBODIMENTS

Referring to FIGS. 1–4, there is illustrated a surgical tool 10 adapted to be locked to the end of a handle assembly 20 in accordance with a first embodiment of the invention. The surgical tool 10 has a tapered entry end 11, a rasp body 12 and a coupling projection 13 provided at the distal end thereof with a coupling recess 14. Referring in particular to FIG. 4, the recess 14 includes an upper lobe 15 which defines a finger 16, the lobe 15 being coupled by means of a shoulder 17 to a lower lobe 18 which defines a finger 19.

The handle assembly 20 includes an elongated body 21 which is solid at one end thereof and is generally channel-shaped along the remainder of the length thereof, including a rectangular end wall 22 integral at the opposite side edges thereof with parallel, depending side walls 23 and 24. Fixedly secured to the body 21 at the solid rear end thereof is an enlarged hand rest 25. The forward ends of the side walls 23 and 24 are, respectively, tapered as at 26 and 28, the side wall 24 having a relief notch 27 formed therein, the side wall 24 also being provided with enlarged, rectangular lightening notches 29 and 30 cut therefrom, while the side wall 23 has a recess 31 cut in the lower edge thereof. The solid rear end of the body 21 may also be provided with lightening bores 32 extending side-to-side therethrough. Extending through the solid rear end of the body 21 from top to bottom between the lightening bores 32 is an internally threaded bore 33, the opposite ends of which communicate respectively with elongated oval recesses 34 and 35, respectively formed in the upper and lower surfaces of the body 21, for receiving one end of an auxiliary handle 36 which is provided with a stud threadedly engageable in the bore 33. The underside of the end wall 22 is relieved, as at 37, adjacent to the front end thereof, this front end defining a fixed jaw 38 provided with an upwardly projecting lip 39 at the distal end thereof.

The handle assembly 20 is also provided with a movable jaw 40, which is disposed between the tapered forward edges of the side walls 23 and 24 and is coupled thereto for pivotal movement relative to the fixed jaw 38 about a pivot pin 41 which extends through a complementary bore adjacent to one end of the movable jaw 40 and also through complementary bores in the side walls 23 and 24. The movable jaw 40 is provided with a forwardly and downwardly curved coupling lip 42 at the distal end thereof disposed near the forward end of the body 21. The movable jaw 40 is also provided with an upwardly and rearwardly extending flange 43 of reduced thickness, which is coupled by means of a pivot pin 44 to the forward end of a locking lever 45.

More specifically, the locking lever 45 has a bifurcated forward end 46 which receives between the legs thereof the flange 43 for pivotal coupling thereto. The locking lever 45 is also provided with a handle end 47 and a fulcrum 48 disposed intermediate the forward and handle ends 46 and 47. A pivot pin 49 extends through the fulcrum 48 for pivotally coupling the locking lever 45 to a release lever 50 and, more specifically, the offset forward end 51 thereof. The lever 50 also includes a rearwardly extending handle end 52 and has a fulcrum 53 intermediate the forward and handle ends 51 and 52. Formed through the fulcrum 53 is a circular bore 54 in which is received a cylindrical cam 55. Formed, in turn, through the cam 55 is an eccentric bore 57 which has an axis parallel to, but spaced from, the axis of the bore 54. The cam 55 has a radial bore 58 therethrough which receives a pin 59, access to the cam 55 being provided by a pin hole 59a in the fulcrum of the release lever 50.

The handle assembly 20 is also provided with an adjustment knob 60 having an elongated shaft 60a which is received through complementary aligned bores in the side walls 23 and 24 and also through the bore 57 of the cam 55, the shaft 60a having a radial bore therethrough receiving the pin 59 for fixing the shaft 60a to the cam 55. One end of the shaft 60a projects outwardly beyond the side wall 23 and is provided with a circumferential groove which receives an E-clip 61 which is, in turn, receivable in a recess 62 in the outer surface of the side wall 23 (FIG. 5). Integral with the shaft 60a at its other end is an enlarged cylindrical head 63 which is disposed outside the side wall 24 and which cooperates with the clip 61 to retain the adjusting knob 60 in place. Formed through the head 63 parallel to the axis of the shaft 60a is a bore 64 having an enlarged cylindrical counterbore 65 in which is seated a helical compression spring 66 which bears against a detent ball 67 also received in the counterbore 65, for urging the detent ball 67 outwardly into engagement in one of a plurality of circumferentially spaced-apart detent recesses 68 formed in the outer surface of the side wall 24, as can best be seen in FIG. 6. The bore 64 also serves as a position indicator.

In operation, the adjustment knob 60 is rotatable about the axis of the shaft 60a among a plurality of adjustment positions, in each of which it is resiliently retained by means of the detent ball 67 and the detent recesses 68. Rotation of the adjustment knob 60 effects a corresponding rotation of the cam 55 pinned thereto, the cam 55 being freely rotatable within the bore 54 in the release lever 50. Because the cam 55 is mounted eccentrically on the shaft 60a, the position of the fulcrum 53 of the release lever 50 shifts slightly as the adjustment knob 60 is rotated, effecting a corresponding shift in the positions of the locking lever 45 and the movable jaw 40, two such positions being respectively illustrated in solid and broken line in FIG. 3.

It will be appreciated that the levers 45 and 50 cooperate with the cam 55 and the pivot pins 44 and 49 to define a linkage for effecting manual operation of the movable jaw 40 between locking and unlocking conditions relative to the fixed jaw 38, the locking condition being illustrated in FIGS. 1, 2, and 4. More specifically, it can be seen that, since the pivot pin 41 of the movable jaw 40 and the shaft 60a of the adjustment knob 60 are fixed relative to the handle body 21, when the handle end 47 of the locking lever 45 is moved downwardly from the position shown in FIG. 2, it will serve to pull the fulcrum 48 and pivot pin 49 down, thereby pivoting the release lever 50 in a counterclockwise direction about the axis of the adjustment knob shaft 60a and simultaneously pivoting the fixed movable jaw 40 in a clockwise direction about the axis of the pivot pin 41 to an unlocking position, wherein the movable jaw 40 is pulled up into the recess 37 on the underside of the handle body end wall 22. In this unlocking or retracted position of the movable jaw 40, the distance between the lips 39 and 42 of the jaws 38 and 40 is at a minimum for facilitating coupling of the surgical tool 10 to the handle assembly 20.

Referring in particular to FIG. 3, when the jaws are in this unlocking condition, the lip 39 of the fixed jaw 38 is inserted in the lobe 15 of the coupling recess 14 and the surgical tool 10 is then tilted down to the position illustrated in FIGS. 1 and 2, the finger 19 easily clearing the lip 42 over retracted movable jaw 40. The handle end 47 of the locking lever 45 is then manually moved up toward the body 21 to bring the linkage to its locking condition illustrated in FIGS. 1 and 2. As the parts are moved to this locking condition, the movable jaw 40 is pivoted in a counterclockwise direction, extending the lip 42 into the lobe 18 of the coupling recess 14, effectively spreading the jaws 38 and 40 securely to grip the coupling projection 13 of the surgical tool 10 and locking it to the handle assembly 20. As the locking lever 45 pivots back to the locking condition, the pivot pin 49 is pushed back up above the plane P of the axes of the pivot pin 41 and the adjustment knob shaft 60a, effecting an over-center action which serves to retain the linkage in its locking condition.

Once the parts have been thus locked together, it may require considerable force on the locking lever 45 to free the surgical tool 10 because of this over-center action. Accordingly, the release lever 50 is provided with an elongated handle which defines a first-class lever of considerable leverage, so that depression of the handle 52 toward the body end wall 22 to pivot the release lever 50 in a counterclockwise direction, as viewed in FIG. 2, will drop the pivot pin 49 back below the over-center plane P, shifting the linkage back to its unlocking condition and releasing the surgical tool 10.

It is a significant aspect of the invention that the locking handle assembly 20 is adjustable by means of the adjustment knob 60, as was described above, so that the jaws 38 and 40 can securely lock in coupling recesses of varying sizes, which variation may be by design or may be the result of tolerance variations in the parts. Thus, it can be seen that, by rotation of the adjustment knob 60, the position of the movable jaw 40 in each of the locking and unlocking conditions is shifted slightly, thereby also slightly shifting the distance between the lips 39 and 42 of the jaws 38 and 40 in their locking condition. In particular, as the adjustment knob 60 is rotated the pivot pin 49 is shifted, thereby shifting the locking lever 45 and the pivot pin 44. Thus, the distance between the axes of the pivot pin 44 and the fixed adjustment knob shaft 60a changes, resulting in corresponding movement of the lip 42 of the movable jaw 40. Thus, when the locking lever 45 is actuated between locking and unlocking conditions, the corresponding positions between which the locking jaw 40 is moved are different for different settings of the adjustable knob 60. The cooperation of the detent ball 67 and the detent recesses 68 serves to retain the adjustment knob 60 in its selected adjustment position. In the illustrated embodiment, five such detent positions are shown, but it will be appreciated that a different number of positions could be provided if desired.

Referring now also to FIGS. 8–13, there is illustrated another embodiment of the present invention including a surgical tool 70 and a handle assembly 80. The surgical tool 70 includes a rasp body 71 having a coupling projection 72 at the rear end thereof. The coupling projection 72 is a body having parallel flat sides and arcuate bottom and top surfaces 73 and 74, the top surface 74 having an arcuate coupling notch 75 formed therein.

The handle assembly 80 includes an elongated body 81 having a flat rectangular end wall 82 and a pair of parallel side walls 83 and 84, respectively depending from the opposite side edges of the end wall 82. The side walls 83 and 84 are, respectively, provided with upwardly and forwardly inclined portions 83a and 84a at the forward end thereof, those portions being joined by an inclined front wall 85 which cooperates with the inclined portions 83a and 84a to define a fixed jaw 86 of the handle assembly 80. The walls 82–84 are joined at the rear end of the body 81 by a rear wall 87, to which is fixedly secured a hand rest 88. Recesses 89 and 89a are, respectively, formed in the side walls 83 and 84 intermediate their forward and rearward ends and adjacent to the lower edges thereof, as can best be seen in FIGS. 10–12.

The handle assembly 80 also includes a movable jaw 90 disposed between the side walls 83 and 84 adjacent to their forward ends and pivotally coupled thereto by a pivot pin 91 disposed adjacent to one end of the jaw 90. The distal end of the jaw 90 is provided with a depending, part-cylindrical lip or projection 92 dimensioned for mating engagement in the coupling notch 75 of the surgical tool 70, as will be explained more fully below. The jaw 90 is provided adjacent to its pivot end with an upwardly and rearwardly extending reduced thickness flange 93, which is pivotally coupled by a pivot pin 94 to the bifurcated forward end 96 of a locking lever 95. The locking lever 95 has a rearwardly extending handle end 97 and is provided intermediate its ends with a fulcrum 98, which is coupled by means of a pivot pin 99 to a release lever 100. More specifically, the release lever 100 has an offset forward end 101 coupled to the pivot pin 99 and a rearwardly extending handle end 102 and a fulcrum 103 disposed intermediate the ends 101 and 102. A cylindrical bore 104 extends laterally through the fulcrum 103 and receives therein a cylindrical cam 105 which, in turn, has a cylindrical bore 107 formed eccentrically therethrough. The cam 105 also has a radial bore 108 therein for receiving an associated pin 109, which is receivable through a complementary access hole 106 in the fulcrum 103 to pin the cam 105 to an adjustment knob 110.

More specifically, referring in particular to FIGS. 10–13, the adjustment knob 110 has an elongated cylindrical shaft 110a which extends through complementary bores in the side walls 83 and 84 at the locations of the recesses 89 and 89a, and also extends through the eccentric bore 107 in the cam 105, the shaft 110a having a radial bore therethrough for receiving the pin 109 to fixedly secure the shaft 110a to the cam 105. One end of the shaft 110a is provided with a circumferential groove which receives a frustoconical spring-type E-clip 111, which is receivable in the recess 89. The other end of the shaft 110a is provided with an enlarged, circular, relatively flat head 113, which is receivable in the recess 89a for cooperation with the clip 111 to retain the adjustment knob 110 in place. The head 113 has a locating bore 114 therethrough to serve as a rotational positioning indicator, and also has a diametrical slot 115 extending thereacross for receiving an associated screwdriver blade or the like to effect rotation thereof. The inner surface of the head 113 has a plurality of circumferentially spaced-apart detent recesses 116 formed therein (FIG. 13) for receiving a detent ball 117, which is mounted in a complementary recess in the side wall 84 of the body 81 for retaining the adjustment knob 110 in any a plurality of rotational positions. It will be appreciated that the spring clip 111 accommodates a slight axial movement of the adjustment knob 110 to permit rotation of the adjustment knob 110 among its several adjustment positions, while providing an axial force biasing the adjustment knob to its adjustment position. FIG. 13 shows 12 detent positions, but it will be appreciated that any desired number could be provided.

The handle assembly 80 operates in substantially the same manner as was described above in connection with the handle assembly 20. Thus, the locking lever 95 undergoes a compound pivotal/translational movement between locking and unlocking conditions in which, respectively, the axis of the pivot pin 99 is disposed above and below a plane P' containing the axes of the pivot pin 91 and the shaft 110a, as viewed in FIG. 9, for effecting corresponding movements of the movable jaw 90. In the locking condition (not shown) the handle ends 97 and 102 of the levers 95 and 100 are disposed in contact with each other or very closely adjacent to each other. In the unlocking condition (not shown) the handle end 102 is disposed against the body end wall 82, while the handle end 97 is inclined downwardly from the body 81. The parts are illustrated in FIGS. 8 and 9 in an intermediate position.

In use, the linkage formed by the levers 95 and 100 is moved to the unlocking condition, in which the distal ends of the fixed and movable jaws 86 and 90 are spaced apart the maximum amount. In this configuration, the coupling projection 72 of the surgical tool 70 is inserted between the jaws 86 and 90 and the projection 92 is aligned with the coupling notch 75. The linkage is then moved to the locking condition, moving the projection 92 into the coupling notch 75 and firmly clamping the coupling projection 72 against the inclined front wall 85 of the fixed jaw 86. As was explained above, during this movement the linkage undergoes an over-center action which effectively locks the parts in their locking condition and inhibits accidental movement therefrom. In order to unlock the surgical tool 70 from the handle assembly 80, the handle end 102 of the release lever 100 is depressed, i.e., moved up toward the body wall 82, thereby shifting the pivot pin 99 back down below the over-center plane P' and moving the linkage to the unlocking condition.

The adjustment knob 110 is rotatable by means of a screwdriver or the like, to shift the position of the fulcrum 103 of the release lever 100 by the camming action of the eccentric cam 105, in the same manner as was described above in connection with the handle assembly 20, for thereby effecting a similar shifting of the position of the movable jaw 90 in the locking and unlocking conditions relative to the fixed jaw 86, for the same purpose as was explained above in connection with the handle assembly 20.

From the foregoing, it can be seen that there has been provided an improved locking handle assembly for a surgical tool which is adjustable among a number of conditions so as to accommodate size variations in the parts, while assuring a firm and rigid locking of the surgical tool 70 on the handle assembly 80.

We claim:

1. An adjustable locking handle for a surgical tool comprising: an elongated body having a tool end; a fixed jaw on said body adjacent to said tool end; a movable jaw; a pivot on said body adjacent to said tool end having a fixed pivot axis fixed relative to said body, said pivot being coupled to said movable jaw for pivotal movement of said movable jaw between locking and unlocking conditions relative to said fixed jaw; a manually operable locking linkage mounted on said body, said linkage including a cam follower surface, a lever pivotally movable relative to said body about a movable pivot axis, and a locking member coupled to said lever and to said movable jaw for effecting movement of said movable jaw between the locking and unlocking conditions thereof; and a cam member carried by said body for rotation relative to said body about a rotation axis fixed on said body and having said movable pivot axis eccentrically disposed on said cam member parallel to said rotation axis, said cam member being disposed for camming engagement with said cam follower surface.

2. The handle of claim 1, wherein said lever is a first lever and said locking member includes a second lever, said second lever being pivotally connected to each of said first lever and said movable jaw.

3. The handle of claim 1, wherein said lever has a bore therethrough defining said cam follower surface, said cam member being disposed in said bore for moving said lever in response to rotation of said cam member.

4. The handle of claim 3, and further comprising a shaft mounted on said body for rotation about said rotation axis, said cam member being received over said shaft eccentrically with respect to said rotation axis.

5. The handle of claim 4, wherein said shaft has an enlarged head at one end thereof, and further comprising detent means coupled between said head and said body for resiliently retaining said cam member in each of a plurality of different rotational positions.

6. The handle of claim 5, wherein said head projects outwardly beyond said body, said detent means including a plurality of detent recesses in said body disposed adjacent to said head, and further comprising a spring-biased detent ball carried by said head for engagement successively in said detent recesses as said cam member is rotated.

7. The handle of claim 5, wherein said body has an outer surface and said detent means includes a recess formed in said outer surface, and a detent ball disposed in said recess and projecting therefrom, said head being disposed in said recess and having an outer surface substantially flush with said outer surface of said body, said head having a plurality of detent recesses therein disposed for successive engagement with said detent ball as said cam member is rotated, and means biasing said head into engagement with said detent ball.

8. The handle of claim 4, and further comprising sa radial coupling member fixedly securing said cam member to said shaft.

9. In combination: a surgical tool having first and second coupling portions thereon; and an adjustable locking handle for said tool, said handle including an elongated body having a tool end, a fixed jaw and a movable jaw disposed on said body adjacent to said tool end for respective engagement with said first and second coupling portions, a pivot on said body having a fixed pivot axis, said pivot being fixed relative to said body and coupled to said movable jaw for pivotal movement of said movable jaw between locking and unlocking conditions relative to said fixed jaw, a manually operable locking linkage mounted on said body, said linkage including a cam follower surface, a lever pivotally movable relative to said body about a movable pivot axis, and a locking member coupled to said lever and to said movable jaw for effecting movement of said movable jaw between the locking and unlocking conditions thereof, and a cam member carried by said body for rotation relative to said body about a rotation axis fixed on said body and having said movable pivot axis eccentrically disposed thereon parallel to said rotation axis, said cam member being disposed for camming engagement with said cam follower surface.

10. The combination of claim 9, and further comprising a shaft mounted on said body for rotation about said rotation axis, said cam member being received over said shaft eccentrically with respect to said rotation axis.

11. The combination of claim 10, wherein said shaft has an enlarged head at one end thereof, and further comprising detent means coupled between said head and said body for resiliently retaining said cam member in each a plurality of different rotational positions.

12. The combination of claim 11, wherein said head projects outwardly beyond said body, said detent means including a plurality of detent recesses in said body disposed adjacent to said head, and further comprising a spring-biased detent ball carried by said head for engagement successively in said detent recesses as said cam member is rotated.

13. The combination of claim 11, wherein said body has an outer surface and said detent means includes a recess formed in said outer surface, and a detent ball disposed in said recess and projecting therefrom, said head being disposed in said recess and having an outer surface substantially flush with said outer surface of said body, said head having a plurality of detent recesses therein disposed for successive engagement with said detent ball as said cam member is rotated, and means biasing said head into engagement with said detent ball.

* * * * *